United States Patent
Yue et al.

(10) Patent No.: US 10,537,540 B2
(45) Date of Patent: Jan. 21, 2020

(54) PHARMACEUTICAL COMPOSITION FOR PROMOTING NERVE INJURY RESTORATION AND APPLICATION THEREOF

(75) Inventors: Maoxing Yue, Beijing (CN); Honggui Wan, Jiangsu (CN); Tongge Huang, Jiangsu (CN)

(73) Assignee: Tongge Huang, Nanjing (CN)

( * ) Notice: Subject to any disclaimer, the term of this patent is extended or adjusted under 35 U.S.C. 154(b) by 290 days.

(21) Appl. No.: 14/418,009

(22) PCT Filed: Aug. 23, 2012

(86) PCT No.: PCT/CN2012/080517
§ 371 (c)(1),
(2), (4) Date: Jan. 28, 2015

(87) PCT Pub. No.: WO2014/019268
PCT Pub. Date: Feb. 6, 2014

(65) Prior Publication Data
US 2015/0335627 A1    Nov. 26, 2015

(30) Foreign Application Priority Data
Aug. 1, 2012 (CN) .......................... 2012 1 0272724

(51) Int. Cl.
*A61K 31/198* (2006.01)
*A61K 31/4415* (2006.01)

(52) U.S. Cl.
CPC ........ *A61K 31/198* (2013.01); *A61K 31/4415* (2013.01)

(58) Field of Classification Search
None
See application file for complete search history.

(56) References Cited

U.S. PATENT DOCUMENTS

| | | | | |
|---|---|---|---|---|
| 6,294,520 B1 * | 9/2001 | Naito | ....................... | A61K 8/44 514/1.2 |
| 2003/0077564 A1 * | 4/2003 | Brewer | ................ | A61K 9/0085 435/1.1 |
| 2009/0215727 A1 * | 8/2009 | Douglas | ............... | A61K 31/675 514/89 |
| 2013/0143836 A1 * | 6/2013 | Yue | ...................... | A61K 31/197 514/52 |

FOREIGN PATENT DOCUMENTS

| CN | 101912394 A | * | 12/2010 | ........... A61K 31/197 |
|---|---|---|---|---|
| WO | WO 2012016408 A1 | * | 2/2012 | ........... A61K 31/197 |

OTHER PUBLICATIONS

Evans, The Anatomical Record, 2001, vol. 263, No. 4, pp. 396-404.*
Mayo Clinic, Transverse Myelitis: Symptoms and Causes, https://www.mayoclinic.org/diseases-conditions/transverse-myelitis/symptoms-causes/syc-20354726 accessed Aug. 7, 2018 (Year: 2018).*
Jacob et al., "An Approach to the Diagnosis of Acute Transverse Myelitis", Seminars in Neurology, 2008, vol. 28, No. 1, pp. 105-120 (Year: 2008).*
Mayo Clinic, Transverse Myelitis: Diagnosis and Treatment, https://www.mayoclinic.org/diseases-conditions/transverse-myelitis/diagnosis-treatment/drc-20354730 accessed Aug. 7, 2018 (Year: 2018).*

* cited by examiner

*Primary Examiner* — Jeffrey S Lundgren
*Assistant Examiner* — Stephanie K Springer
(74) *Attorney, Agent, or Firm* — Oliff PLC

(57) ABSTRACT

A pharmaceutical composition for promoting nerve injury restoration and a use thereof are disclosed. Each unit of the pharmaceutical composition contains 0.5 to 8 g of L-ornithine, 1 to 5 g of aspartic acid, 3 to 10 g of arginine and 3 to 10 g of vitamin $B_6$. The pharmaceutical composition can significantly promote recovery of the spinal nerve function, and particularly has a good therapeutic effect on acute myelitis.

12 Claims, No Drawings

PHARMACEUTICAL COMPOSITION FOR PROMOTING NERVE INJURY RESTORATION AND APPLICATION THEREOF

This application is the U.S. national phase of International Application No PCT/CN2012/080517 filed on Aug. 23, 2012 which designated the U.S. and claims priority to Chinese Application No. 201210272724.2 filed on Aug. 1, 2012, the entire contents of each of which are hereby incorporated by reference.

TECHNICAL FIELD

The present invention relates to the field of medicines and health care products, and particularly to a pharmaceutical composition for promoting nerve injury restoration and a use thereof.

RELATED ART

In 1960s, scientists confirmed for the first time that the mammalian central nervous system has an endogenous restoration property, the neuronal axons and main branches of the adult brain and spinal cord that are subject to some degree of injury can be restored, and the birth of new neurons in the brains of adult bird, non-human primates and humans is called nerve restoration. Nerve restoration drugs refer to those drugs that promote neuronal restoration by directly acting on the neural stem cells in human or animal brains and have the effect of increasing the brain neurons. Such nerve restoration drugs can be used for the treatment of neurological diseases caused by neural degeneration or injury.

To date, there are many drugs for treating spinal cord injury, but only methylprednisolone is widely used as its effect in the treatment of spinal cord injury has been confirmed. Many other drugs are still in the experimental stage, and with the development of fundamental research on the mechanism of spinal cord injury, some new drugs or existing drugs are continuously proved to be effective in the treatment of experimental spinal cord injury. However, due to various reasons, these drugs cannot enter the clinical trial stage. As a result, although there are many new drugs, such drugs cannot be widely used clinically. In addition, most drugs merely acts on a certain aspect of the spinal cord injury, while the spinal cord injury involves many injury aspects and mechanisms, so the effects of these new drugs are limited. Moreover, the unique therapeutic window characteristics after the spinal cord injury also affect the development of drugs. Currently, in order to treat the spinal cord injury, different drugs are often used in combination, which provides a better therapeutic effect than that of a single drug. In researches of factors promoting nerve restoration, the first reported nerve cell regulating factor whose molecular structure has been clearly explained is nerve growth factor (NGF). In addition, researches are also focused on gangliosides and basic fibroblast growth factor (bFGF), which have been separately proved to have nerve growth promoting effects of different levels. Current researches and applications mainly focus on single factors, but the described factors have very limited effects on nerve restoration, the therapeutic effect is undetermined, and the cost is high, so the factors cannot be widely used clinically. Currently, clinical researches and applications of substitutes and inducers of nerve growth factors and neurotrophic factors make slow progress abroad, and there is no reliable drug for promoting nerve injury restoration up to now. Therefore, how to promote nerve restoration after injury to restore the functions has become the focus of research.

Acute myelitis refers to a type of non-specific inflammatory lesions in the spinal cord, which always occurs after infection, where the inflammation often involves gray and white matter of several spinal segments and surrounding meninges, and the thoracic spinal cord is the most susceptible to experiencing symptoms of transverse spinal cord injury. The clinical manifestation is characterized in limb paralysis below the level of the lesion, sensory tract dysfunction and difficulties with urination and defecation. Early treatment, intensive care and early rehabilitation training are very important for prognosis of acute myelitis. The position of the involved segments of spinal cord is one of the main factors that influence the therapeutic effect. The higher the segments of spinal cord are, the poorer the therapeutic effect is. Currently, treatment methods mainly include: immunosuppressive therapy, mainly including corticosteroids, immunoglobulin, etc.; and symptomatic treatment, mainly including nerve nutrition, anti-infection and support therapy. However, the application of the existing treatment methods is limited due to great side effects and non-significant therapeutic effects.

Amino acids are the most basic substances that constitute organism proteins are involved in vital activities, are the basic units constitute protein molecules in organisms, and are closely associated with the vital activities of organisms. Amino acids have special physiological functions in antibodies, and are one of the indispensable nutrients in organisms. Amino acids have the following functions in the human body through metabolism: (1) synthesis of tissue proteins; (2) being changed into ammonia containing substances such as acids, hormones, antibodies and creatine; (3) being converted into carbohydrates and fats; (4) being oxidized into carbon dioxide, water and urea, with energy generated. L-ornithine is a non-protein amino acid, is mainly involved in urea cycle in organisms, plays an important role in discharge of ammonia nitrogen from the body, and together with aspartic acid, can enhance the detoxification function of the liver, quickly lower the blood ammonia, and promote liver cell restoration and regeneration. Therefore, amino acids existing in the human body not only provide important raw materials for synthesis of proteins, but also provide a material basis for promoting the growth, carrying out normal metabolism and sustaining life. A lack or depletion of one of the amino acids in the human body can impede the normal metabolism of the human body, or even lead to various diseases or the end of vital activities. Therefore, amino acids have the functions of nourishing the nerves and promoting enzyme metabolism, neurotransmitter production, and cell function restoration.

B vitamins are water-soluble vitamins, include vitamin $B_1$, vitamin $B_2$, vitamin $B_6$, vitamin $B_{12}$, nicotinic acid, pantothenic acid, folic acid, etc., and are indispensable substances for promoting metabolism in vivo and converting carbohydrates, fats and proteins into heat. B vitamins have synergistic effects, and can regulate metabolism, maintain the health of skin and muscles, improve the functions of the immune system and the nervous system, promote the cell growth and division, and facilitate the recovery of nerve function. Vitamin $B_1$ has a good effect on nerve tissue and mental state, and can help maintain mental alertness and emotional stability, promote blood circulation, assist in hydrochloric acid production, blood formation and carbohydrate metabolism, contribute to human perception, and help the brain to function at its best; and also plays a positive role in energy metabolism, growth, appetite and learning ability. Vitamin $B_{12}$ is stored in the liver, but is easily excreted though urine; it maintains normal body growth and red blood cell growth, and helps maintain the health of the nervous system.

$B_6$ may be the most important one among all the B vitamins. $B_6$ in the muscles of the human body accounts for 70% to 80% of that in the whole body. $B_6$ plays a key role in metabolism of proteins, lipids and carbohydrates. Therefore, a person who lost a large amount of $B_6$ will have amino acid metabolism disorders. Vitamin $B_6$ is a coenzyme for many important enzyme systems in the body, participates in physiological processes such as decarboxylation of amino acids, synthesis of tryptophan, metabolism of sulfur-containing amino acids and metabolism of unsaturated fatty acids, and is a necessary nutrient for normal development of animals and reproduction of bacteria and yeasts. In addition, vitamin $B_6$ is also a natural diuretic and thus can be used for detoxification. By means of intravenous infusion of 5 g of vitamin $B_6$, about 380 mL of urine can be induced. Vitamin $B_6$ is a coenzyme for amino acid metabolism in the human body, neurotransmitters γ-aminobutyric acid (GABA) and glutamic acid (Glu). It is known that more than 60 enzymes in the liver require participation of vitamin $B_6$, and therefore vitamin $B_6$ plays a very important role in promoting the normal enzyme metabolism in the body. Vitamin $B_6$ can maintain the level of neurotransmitters γ-aminobutyric acid (GABA) and glutamic acid (Glu). In addition, vitamin $B_6$ has a short half life in the body and is quickly excreted.

After spinal cord injury, endogenous antioxidants such as vitamins C and E are significantly reduced or exhausted. Vitamin C has anti-inflammatory and anti-oxidation effects, and due to its small relative molecular weight, can directly enter into cells to directly or indirectly remove oxygen free radicals and block the lipid peroxidation. Vitamin C can also have an anti-oxidation effect by recovering the activity of vitamin E. Vitamin C can promote the biosynthesis of collagen to accelerate healing of tissue injuries; promote the metabolism of amino acids tyrosine and tryptophan to prolong the life of the body; improve the stress resistance and immunity of the body against the external environment; improve the utilization of iron, calcium and folic acid; and improve the metabolism of fats and lipids, especially cholesterol, to prevent cardiovascular diseases. EPC-K1 is a recently synthesized derivative of vitamin C and vitamin E, and can independently remove water-soluble and lipid-soluble free radicals. Katoh et al. found that the use of EPC-K1 in a rat spinal cord injury model can significantly block lipid peroxidation and remove free radicals (water-soluble+lipid-soluble) after spinal cord injury, thereby achieving the effect of protecting the injured spinal cord.

SUMMARY

An objective of the present invention is to provide a pharmaceutical composition for promoting nerve injury restoration, which is a composition of complex amino acids and vitamins designed for patients with spinal cord diseases, and can promote nerve restoration to restore most or all of the functions of nerves and muscles below the lesion segment, so that the patients can basically live independently.

Another objective of the present invention is to provide a use of the pharmaceutical composition.

The objectives of the present invention are achieved by means of the following technical solutions:

A pharmaceutical composition for promoting nerve injury restoration is provided, where each unit of the pharmaceutical composition contains: 0.5 to 8 g of L-ornithine, 1 to 5 g of aspartic acid, 3 to 10 g of arginine, 3 to 10 g of vitamin $B_6$, with the rest being an excipient and/or other ingredients.

In accordance with the pharmaceutical composition, each unit of the pharmaceutical composition further contains one or more of the following substances: isoleucine, leucine, lysine, methionine, phenylalanine, threonine, tryptophan, valine, histidine, glycine, alanine, proline, asparagine, cysteine, glutamic acid, serine, tyrosine, vitamin $B_1$, vitamin $B_2$, pantothenic acid, biotin, folic acid, vitamin $B_{12}$ and vitamin C.

In accordance with the pharmaceutical composition, in each unit of the pharmaceutical composition, the contents of the amino acids are: 3 to 10 g of isoleucine, 5 to 15 g of leucine, 3 to 10 g of lysine, 0.5 to 3 g of methionine, 0.5 to 3 g of phenylalanine, 3 to 10 g of threonine, 0.5 to 3 g of tryptophan, 5 to 15 g of valine, 3 to 8 g of histidine, 3 to 8 g of glycine, 3 to 10 g of alanine, 3 to 8 g of proline, 0.1 to 3 g of asparagine, 0.1 to 3 g of cysteine, 3 to 10 g of glutamic acid, 0.5 to 5 g of serine, and 0.1 to 3 g of tyrosine; and the contents of the B vitamins are: 1 to 2 mg of vitamin $B_1$, 1 to 2 mg of vitamin $B_2$, 3 to 5 mg of pantothenic acid, 0.1 to 0.2 mg of biotin, 0.1 to 0.4 mg of folic acid, 2 to 6 μg of vitamin $B_{12}$, and 1 to 3 g of vitamin C.

In accordance with the pharmaceutical composition, the pharmaceutical composition contains a combination of any one or more of B vitamins and vitamin C, and preferably, a combination of vitamin C and vitamin $B_6$.

In accordance with the pharmaceutical composition, the pharmaceutical composition further contains a suitable amount of 5% glucose and sodium chloride injection or 0.9% sodium chloride injection.

In accordance with the pharmaceutical composition, the pharmaceutical composition can be in any pharmaceutical dosage form, and is preferably in the form of granules, tablets, capsules or injections.

A use of the pharmaceutical composition in preparing a drug and/or health care product for promoting nerve injury restoration is provided.

In accordance with the use, the drug for promoting nerve injury restoration is a drug for treating spinal cord injury.

In accordance with the use, the spinal cord injury disease is acute myelitis.

The present invention has the following beneficial effects:

In the pharmaceutical composition of the present invention, amino acids and vitamins are used as raw materials, which, after being scientifically combined, not only can provide nutritional support for patients and enhance the immunity of the body, but also can nourish the nerves and promote enzyme metabolism, neurotransmitter production and cell function restoration. Compared with the existing drugs for treating diseases of spinal cord injury, the pharmaceutical composition of the present invention has the advantages of confirmed therapeutic effect, fewer side effects, and on the like. As for clinical patients with secondary myelitis, on the basis of comprehensive treatment, a new therapy using a combination of complex amino acids and large-dose $B_6$ surely has the efficacies of diuresis, detoxification, anti-oxidation, reducing exudate, promoting metabolism of enzymes and protecting functions of brain and nervous system. As coenzymes for synthesis of various neurotransmitters, vitamins $B_1$ and $B_6$ have special nervous regulation functions, are easy to be absorbed orally, and have very low toxic and side effects. In view of the above characteristics, vitamins $B_1$ and $B_6$ have a broad application prospect in developing a novel neurotrophic and neuroprotective drug for neurological diseases.

Pharmacological experiments of the composition of the present invention and clinical observations are as follows:

Experiment I: Influence of the Pharmaceutical Composition on Nerve Restoration and Motor Function after Spinal Cord Injury in Rats 1. Experimental materials and methods 1) Modeling and administration methods: 60 clean standard adult healthy, male or female Wistar rats having a weight of 250 to 300 g are selected, injected with 1% sodium pentobarbital (50 mg/kg) intraperitoneally for anesthesia, and fixed in a prone position. Under sterile conditions, T9 and T10 spinous processes are exposed, the vertebral plates are cut off to expose the dura mater, and spinal cord injury models are established by using the weight drop method (10 g*4 cm). The criteria of successful establishment of the spinal cord injury models are that: spinal cord tissue edema and subdural hyperemia and hemorrhage are observed after hitting, and for the behavioral test at 24 h after surgery, the BBB (Basso-Beattie-Bresnahan) score is less than or equal to 1. Hemostasis and suture are performed in time after surgery, warming and anti-infection treatment are enhanced, massaging of the bladder is performed twice per day, and povidone-iodine disinfection on the perineum is performed until recovery of the bladder function. After successful modeling, 60 rats are randomly divided into two groups: a saline group and a pharmaceutical composition treatment group. After surgery, the treatment group is administered intraperitoneally with a pharmaceutical composition injection at 2 mL/kg once per day for 4 weeks. The saline group is injected with saline of the same volume intraperitoneally. The composition of the present invention used in this experiment is prepared according to Embodiment 3.

2) Inclined plate test: The rat is horizontally placed on an improved Rivlin inclined plate with the head towards the left, the angle is gradually increased from the horizontal position, the maximum angle at which the animal can stay on the plate for 5 s without falling off is taken as the standard for evaluation, the test is repeated three times, and the average value is taken as the final result. The two groups of rats are respectively subjected to the test at 1 d, 2 d, 3 d, 1 w, 2 w, 3 w and 4 w after surgery.

3) BBB motor scoring: The motor function of the two groups of rats are scored by using the double-blind method, the animal is placed on a flat but not smooth desktop in light, the activities of each joints of the hind legs are observed, and the motor function is scored. The rat is scored once before injury, and is respectively at 1 d, 2 d, 3 d, 1 w, 2 w, 3 w and 4 w after modeling, and the detection is performed three times, and the results are averaged. The score mainly reflects the recovery of the motor function, normal rat can be give the highest score (21), the rat with the most serious injury is 0.

4) Selection of tissue and preparation of sections: The two groups of rats are respectively anaesthetize at three time points (I h, 48 h and 72 h) after surgery, about 200 mL of heparin saline is infused through the left ventricle until a supernatant flows out, and then about 200 mL of 4% paraformaldehyde is infused for fixation. Spinal cord tissue having a length of about 8 mm with the injury as the center is taken and fixed with 4% paraformaldehyde for 24 h. After routine paraffin embedding, serial sections are cut at a thickness of 5 μm, and are stained with routine hematoxylin-eosin staining, each sample being cut into 25 sections.

5) Immunohistochemical staining: The expression of NF is detected by using SuperPicture immunohistochemical staining. The working concentration of the anti-NF primary antibody is 1:400, and a ready-to-use $2^{nd}$ generation immunohistochemistry broad spectrum kit SuperPicTure (Mouse/Rabbit KIT, Zymed repackaged) is used. A DAB color kit (DAB-0031) is used. The staining results are observed under an optical microscope, and the immune positive cells are stained to be brownish yellow or dark brown. For each section, 10 different visual fields are selected under the optical microscope at a magnification of 400 times, and a pathological image analyzer and Leica QWin image analysis software are used. As for the sections stained in the same batch, first, the same standard is set according to the staining gray value, and then the average gray value of neurofilament (NF) is calculated according to the background color of staining. The gray value can indirectly reflect the expression activity of cell proteins, the greater the gray value, the lower the expression activity; the smaller the gray value, the higher the expression activity.

2. Main outcome measures: motor function of rat, histopathological observation of the spinal cord, determination of gray value of cells positive for NF staining.

3. Experimental results

1) Histopathological Observation of the Spinal Cord of Rats of Each Group

Results of pathological examination at 72 h after modeling show that the structure of the spinal cord tissue of the rats in the control group is disordered, splinter hemorrhage occurs at many sites and there are cysts formed after hemorrhage necrosis, swelling of nerve cells is obvious, a large number of inflammatory cells aggregate, some nerve cells cannot be recognized, the boundary of the gray and white matter is not clear, the central canal partially disappears or is offset, and the edge of the spinal cord is adhered; the structure of the spinal cord tissue of the rats in the drug group is generally clear, hemorrhage and necrosis are at a low level, fewer cysts are formed, the swelling of the nerve cells is not obvious, the number of infiltrated inflammatory cells is small, the nerve cells are abundant, edema of the white matter occurs, and the edge of the spinal cord cortical area is not clear.

2) Expression of NF

After spinal cord injury, the expression of NF in spinal cord tissue nerve cells gradually increases over time, and first appears in the anterior horn motor neurons, but appears later in the spinal dorsal horn neurons. In the aspect of morphology, the cell body and nucleus of the neurons are both increased. As for the pharmaceutical composition treatment group, an increase in the expression of NF is observed at 1 h after injury, high expression of NF can still be observed at 72 h after injury, and at all time points, the expression level of NF of the pharmaceutical composition treatment group is higher than that of the saline group, and there is a significant difference in NF gray value between the pharmaceutical composition treatment group and the saline group ($P<0.05$). See Table 1.

TABLE 1

Gray values ($\bar{x} \pm s$) of spinal cord cells positive for NF staining around the injury region at different time points of the two groups

| Group | 1 h | 48 h | 72 h |
|---|---|---|---|
| Saline group | 231.42 ± 6.04 | 193.37 ± 4.20 | 189.41 ± 4.86 |
| Drug treatment group | 190.32 ± 4.28* | 185.34 ± 5.71* | 175.80 ± 6.65* |

*Compared with the saline group, $P < 0.05$

3) Behavioral Changes of Rats in Each Group

The BBB scores of the two groups of rats before modeling are both 21, paralysis of both lower limbs occurs after modeling, and all rats have urinary retention. As for spinal shock, the score in the first 3 days is low, and as time passes, the spinal cord functions of the rats are gradually recovered, and the strength of hindlimb muscles is gradually increased, the score at 7 day after injury is increased for both the two groups of rats, and there is a significant difference between the treatment group and the saline group (P<0.05). The results of the inclined plate test after surgery show that from 3 days after injury, the maximum angle of the inclined plate is increased for both the two groups, but there is no significant different between the two groups, while after 7 days, there is a significant difference between the drug group and the control group, P<0.05 (see Table 2 and Table 3), indicating that the pharmaceutical composition injection can significantly promote the recovery of the spinal nerve function after injury.

TABLE 2

Results of the inclined plate test of each group of rats in different time periods after injury ($\bar{x} \pm s$)

| Time after injury | Control group | Drug group |
| --- | --- | --- |
| 1 d | 26.48 ± 2.96 | 30.82 ± 2.32 |
| 2 d | 28.42 ± 1.98 | 32.68 ± 3.23 |
| 3 d | 30.28 ± 2.43 | 36.53 ± 2.35 |
| 1 w | 33.74 ± 2.82 | 41.81 ± 4.32* |
| 2 w | 35.50 ± 5.36 | 45.94 ± 4.76* |
| 3 w | 42.67 ± 5.24 | 53.65 ± 5.26* |
| 4 w | 45.31 ± 5.12 | 56.79 ± 6.25* |

Note:
*Compared with the control group, P < 0.05

TABLE 3

Results of BBB scoring of each group of rats after injury

| Time after injury | Control group | Drug group |
| --- | --- | --- |
| 1 d | 0 | 0 |
| 2 d | 1.24 ± 0.82 | 1.42 ± 0.57 |
| 3 d | 3.03 ± 0.81 | 4.07 ± 1.42 |
| 1 w | 5.29 ± 1.68 | 8.38 ± 1.33* |
| 2 w | 8.24 ± 1.58 | 11.34 ± 1.65* |
| 3 w | 10.59 ± 1.86 | 15.81 ± 2.63* |
| 4 w | 12.68 ± 1.69 | 18.23 ± 2.85* |

Note:
*Compared with the control group, P < 0.05

Experiment II: Clinical Observation Experiments

1. Case Selection Criteria

In accordance with the diagnostic criteria of acute myelitis set forth by the Transverse Myelitis Consortium Working Group (transv working group, TMCWG) in 2002:

(1) progressive sensory, motor, urination and defecation dysfunctions caused by spinal cord injury;

(2) symptoms or signs of bilateral involvement (not necessarily bilaterally symmetric);

(3) having an exact sensory level;

(4) excluding spinal cord compression through imaging examination;

(5) inflammation indicated by increased cells in the cerebrospinal fluid; or if there is no inflammation, MRI manifestations and a cell count of $(2-7)*10^6/L$ also conform to the diagnosis of acute myelitis;

(6) the disease reaching the peak at 4 h to 21 d; and (7) excluding the following: spinal vascular diseases, connective tissue diseases determined by serological tests or clinical confirmation, syphilis, HIV, lymphoma, HTLV21, head MRI abnormality suggestive of myelitis caused by mycoplasma infection or special virus (such as HSV and VZV), diagnosis of multiple sclerosis, previous diagnosis of optic neuritis.

Phases of Acute Myelitis:

With reference to the criteria set forth by the TMCWG: divided into acute phase and recovery phase according to the disease progression:

acute phase: within 3 weeks from pathogenesis;

recovery phase: after 3 weeks from pathogenesis.

2. Research Method:

30 patients with acute myelitis in this group are confirmed according to the clinical manifestation, cerebrospinal fluid, and MR examination. For 18 cases, the lesion is at the thoracic segments; for 6 cases, the lesion is at the lumber segments; for 5 cases, the lesion is at the cervical segments; for 1 case, the lesion is at the sacral segments 15 patients in the treatment group include 9 cases of male and 6 cases of female at the age of 16 to 68, are treated with conventional amounts of corticosteroids, and at the same are administered with the pharmaceutical composition of the present invention (prepared according to Embodiment 5).

15 patients in the control group include 8 cases of male and 7 cases of female at the age of 19 to 72, and are treated with conventional amounts of corticosteroids.

In addition to drug treatment, treatments such as nerve nutrition and symptomatic support as well as intensive care are provided for the patients of the two groups at the same time, so as to prevent and treat complications.

3. Indexes of Therapeutic Effect:

Time for improvement of muscle strength of paralyzed limb to level II;

Time for recovery of sphincter functions;

Time for independent walking

4. Determination of Therapeutic Effect:

Cure: recovered from paralysis to independent walking and good bowel and bladder function;

Remarkable effect: recovered from paralysis to ambulation with a stick;

Improved: improved muscle and bladder function after treatment, but being unable to walk or independently urinate;

Ineffective or worsened: no improvement or worsening in symptoms and signs, dead.

5. Results:

The numbers of cure, remarkable effect, improved, ineffective and dead in the treatment group are 5, 6, 3, 1 and 0 respectively, and the numbers of cure, remarkable effect, improved, ineffective and dead in the control group are 2, 4, 6, 2 and 1. In accordance with the present invention, the nerve function recovery time of the treatment group is significantly less than that of the control group, the cure rate and the remarkable effect rate are significantly higher than those of the control group, and there are significantly differences (see Table 1 and Table 2). The patients in the two groups have no complications and no discomfort during treatment, and no abnormalities occur in vital signs, liver and kidney functions and other biochemical markers and ECG.

TABLE 1

Relationship between the therapeutic effect and the treatment method

| Group | Cure | Remarkable effect | Improved | Ineffective | Dead | Cure and remarkable effect rate |
|---|---|---|---|---|---|---|
| Treatment group | 5 | 6 | 3 | 1 | 0 | 11 (73.3%) |
| Control group | 2 | 4 | 6 | 2 | 1 | 6 (40.0%) |

TABLE 2

Comparison of recovery of the nerve function of the two groups ($\bar{x} \pm s$, d)

| Group | Number of cases | Time for improvement of muscle strength of 2 levels | Time for urination restoration | Time for independent walking |
|---|---|---|---|---|
| Treatment group | 15 | 14.82 ± 7.43 | 10.98 ± 4.05 | 22.34 ± 8.97 |
| Control group | 15 | 24.29 ± 8.41 | 19.63 ± 6.27 | 30.13 ± 4.32 |

BRIEF DESCRIPTION OF THE DRAWINGS

No drawings.

DETAILED DESCRIPTION

The present invention is further described below through embodiments, but the present invention is not limited to the following embodiments.

Embodiment 1: Preparation of Pharmaceutical Composition

A pharmaceutical composition contained the following components: 500 mL of a complex amino acid injection containing 5 amino acids (1.5 g of L-ornithine, 2.5 g of L-aspartic acid, 8.5 g of L-arginine, 3.8 g of L-glycine, 4.6 g of L-threonine); and 8 g of vitamin $B_6$ added to 250 mL of a 0.9% sodium chloride injection.

Embodiment 2: Preparation of Pharmaceutical Composition

A pharmaceutical composition contained the following components: 500 mL of a complex amino acid injection containing 3.5 g of L-ornithine, 2.50 g of aspartic acid, 8.80 g of arginine, 8.80 g of isoleucine, 13.60 g of leucine, 7.51 g of lysine, 1.20 g of methionine, 1.60 g of phenylalanine, 4.60 g of threonine, 1.50 g of tryptophan, 10.60 g of valine, 4.70 g of histidine, 6.30 g of glycine, 8.30 g of alanine, 7.10 g of proline, 0.48 g of asparagine, 0.59 g of cysteine, 5.70 g of glutamic acid, 3.70 g of serine, and 0.67 g of tyrosine; and 5 g of vitamin $B_6$ and 3 g of vitamin C, where the vitamins were added to 250 mL of a 0.9% sodium chloride injection.

Embodiment 3: Preparation of Pharmaceutical Composition

A pharmaceutical composition contained the following components: 500 mL of a complex amino acid injection containing 4.5 g of L-ornithine, 2.80 g of aspartic acid, 8.30 g of arginine, 6.50 g of isoleucine, 12.00 g of leucine, 7.50 g of lysine, 1.60 g of methionine, 1.40 g of phenylalanine, 1.80 g of tryptophan, 10.60 g of valine, 4.80 g of histidine, 6.20 g of glycine, 8.50 g of alanine, 7.10 g of proline, 0.48 g of asparagine, 5.70 g of glutamic acid, 3.70 g of serine, and 0.67 g of tyrosine; and 8 g of vitamin $B_6$, 2 mg of vitamin $B_1$, 1 mg of vitamin $B_2$, 4 mg of pantothenic acid, 0.2 mg of biotin, 0.3 mg of folic acid, 6 μg of vitamin $B_{12}$, and 2 g of vitamin C, where the vitamins were added to 250 mL of a 5% glucose and sodium chloride injection.

Embodiment 4: Preparation of Pharmaceutical Composition

A pharmaceutical composition contained the following components: 500 mL of a complex amino acid injection containing 2.5 g of L-ornithine, 2.50 g of aspartic acid, 8.80 g of arginine, 6.80 g of isoleucine, 11.50 g of leucine, 7.50 g of lysine, 1.60 g of methionine, 1.30 g of phenylalanine, 4.40 g of threonine, 1.70 g of tryptophan, 4.60 g of histidine, 6.30 g of glycine, 8.30 g of alanine, 6.20 g of proline, 0.60 g of asparagine, 0.80 g of cysteine, 5.70 g of glutamic acid, 3.70 g of serine, and 1.10 g of tyrosine; and 1 mg of vitamin $B_1$, 10 g of vitamin $B_6$ and 3 g of vitamin C, where the vitamins were added to 250 mL of a 5% glucose and sodium chloride injection.

Embodiment 5: Preparation of Pharmaceutical Composition

A pharmaceutical composition contained the following components: 500 mL of a complex amino acid injection containing 2.50 g of L-ornithine, 2.50 g of aspartic acid, 8.80 g of arginine, 6.80 g of isoleucine, 11.50 g of leucine, 7.50 g of lysine, 1.60 g of methionine, 1.30 g of phenylalanine, 4.40 g of threonine, 1.70 g of tryptophan, 10 g of valine, 4.60 g of histidine, 6.30 g of glycine, 8.30 g of alanine, 6.20 g of proline, 0.60 g of asparagine, 0.80 g of cysteine, 5.70 g of glutamic acid, 3.70 g of serine, and 1.10 g of tyrosine; and 1 mg of vitamin $B_1$, 1 mg of vitamin $B_2$, 10 g of vitamin $B_6$, 3 mg of pantothenic acid, 0.1 mg of biotin, 0.2 mg of folic acid, 5 μg of vitamin $B_{12}$, and 3 g of vitamin C, where the vitamins were added to 250 mL of a 5% glucose and sodium chloride injection.

Embodiment 6: Description of Specific Cases

Case 1: a male patient, 23 years old, admission number: 201038515. The patient was admitted to the hospital as a patient with acute appendicitis emergency due to more than ten hours of lower abdominal pain on Dec. 22, 2010, and received appendicectomy. In the postoperative night, the patient had numbness at both lower limbs with the right side more serious. The muscle tone of both lower limbs was low, the muscle strength of the right lower limb was level 0, the muscle strength of the left lower limb was level III, the tendon jerk at both sides was (+), and there was no Babinski sign on either side. Lumbar CT (532325) examination was immediately performed and shown pneumatosi in the spinal canal corresponding to T12-L4 and pneumatosis in paraspinal soft tissue. Entire spinal cord MRI (56442) examination indicates thoracic 3 to 9 spinal cord swelling, the signal was heterogeneous, no significant enhancement was observed, and no abnormality was observed in the plain CT scan of the lumbar spine. The patient could not independently urinate on the next day, and urethral catheterization was maintained. The patient had difficulty with defecation. The muscle strength of both lower limbs was level 0, the muscle tone was lowered, there was no pathological sign on either side, the superficial sensibility of right thoracic 6 to 8 and lumbar 2 and below was impaired, and the deep sensibility of lumbar 2 and below was abnormal. The superficial sensibility of the left thoracic 6 to 8 and lumbar 4 and below was impaired, and the deep sensibility of the left lumbar 4 and below was impaired. The abdominal jerk was negative, the knee jerk was suspiciously positive, and the ankle jerk was negative. A lumbar puncture was performed to examine the cerebrospinal fluid, and the report showed: the cerebrospinal fluid was colorless and transparent, Pandy's test was negative, the red blood cell count was $300*10^6/L$, and the white blood cell count was $1*10^6/L$. Postoperative pathological report: acute simple appendicitis (Medical record number 201014312). In accordance with the case history, clinical manifestation, CT, MRI and lumbar puncture examination, the patient was diagnosed to have acute myelitis complicated by appendicitis, and at the early stage, was subjected to comprehensive treatment of hormone therapy, dehydration, nerve nutrition and intravenous immunoglobulin blocking antibodies and early-stage rehabilitation exercises. At the same time, 500 mL of a complex amino acid injection ivgtt qd (containing: 4.50 g of L-ornithine, 2.80 g of aspartic acid, 8.50 g of arginine, 7.50 g of isoleucine, 10.80 g of leucine, 8.50 g of lysine, 1.60 g of methionine, 2.00 g of phenylalanine, 4.60 g of threonine, 1.50 g of tryptophan, 10.50 g of valine, 4.70 g of histidine, 6.30 g of glycine, 8.00 g of alanine, 6.50 g of proline, 0.60 g of asparagine, 0.80 g of cysteine, 5.00 g of glutamic acid, 3.50 g of serine and 1.60 g of tyrosine)+10 g of vitamin $B_6$+1.5 mg of vitamin $B_1$+1.5 mg of vitamin $B_2$+2 g of vitamin C (the vitamins were added to 250 mL of a 0.9% sodium chloride injection) were slowly infused intravenously at a rate of 30 to 60 drops per minute; and the hormone therapy was stopped after 6 weeks. Large-dose vitamin $B_6$ was continuously used, and functional rehabilitation exercises were performed. 2 months later, the amount of vitamin $B_6$ was changed to 3 g qd, and vitamin $B_6$ was used intermittently over a five-day course. The patient could lift the left lower limb off the bed after 2 months, could independently urinate after 4 months, could lift the right lower limb off the bed after 6 months, could walk with assistance after 7 months, and now can independently urinate and defecate. The patient felt good, and now, can independently walk. No toxic or side effects were observed. The patient has been discharged from the hospital for more than 3 months, is in good condition, and can take care of himself. The entire spinal cord MRI examination after discharge showed that the thoracic 3 to 9 spinal cords have recovered.

Case 2: a male patient, 68 years old, admission number: 201233619. The patient was admitted to the hospital as a patient with thoracic 8 vertebral hemangioma, and received a vertebral hemangioma resection surgery in a hospital in Shanghai on October, 2011. Urinary and fecal incontinence occurred after surgery, the muscle tone of both lower limbs was 0, the tendon jerk at both sides was (+), and the patient was diagnosed to have paraplegia after surgery. The patient had received treatment in hospitals in different regions, but the therapeutic effect was not good. The patient was admitted to the hospital for treatment in March, 2012. Admission diagnosis: paraplegia after surgery. 500 mL of a complex amino acid injection ivgtt qd (containing: 4.50 g of L-ornithine, 2.80 g of aspartic acid, 8.50 g of arginine, 7.50 g of isoleucine, 10.80 g of leucine, 8.50 g of lysine, 1.60 g of methionine, 2.00 g of phenylalanine, 4.60 g of threonine, 1.50 g of tryptophan, 10.50 g of valine, 4.70 g of histidine, 6.30 g of glycine, 8.00 g of alanine, 6.50 g of proline, 0.60 g of asparagine, 0.80 g of cysteine, 5.00 g of glutamic acid, 3.50 g of serine and 1.60 g of tyrosine)+3 g of vitamin $B_6$+2 g of vitamin C (the vitamins were added to 250 mL of a 0.9% sodium chloride injection) were slowly infused intravenously at a rate of 30 to 60 drops per minute, and functional rehabilitation exercises were performed. The patient could walk 500 to 600 meters by gripping the handles of a wheelchair. No toxic or side effects were observed. The patient has been discharged from the hospital for more than 1 month, and is in good condition.

Case 3: a male patient, 38 years old, admission number: 201267398. Violent facture of neck vertebrae occurred to the patient due to fall injury on Jun. 16, 2012, and cervical spinal cord injury was caused, resulting in paraplegia. The patient received a cervical vertebral body fixation and cervical spinal cord decompression surgery on Jun. 18, 2012, and was still in paraplegia after the surgery. Various treatments were adopted, but the therapeutic effect was not good. After consultation, 500 mL of a complex amino acid injection ivgtt qd (containing: 4.50 g of L-ornithine, 2.80 g of aspartic acid, 8.50 g of arginine, 7.50 g of isoleucine, 10.80 g of leucine, 8.50 g of lysine, 1.60 g of methionine, 2.00 g of phenylalanine, 4.60 g of threonine, 1.50 g of tryptophan, 10.50 g of valine, 4.70 g of histidine, 6.30 g of glycine, 8.00 g of alanine, 6.50 g of proline, 0.60 g of asparagine, 0.80 g of cysteine, 5.00 g of glutamic acid, 3.50 g of serine and 1.60 g of tyrosine)+5 g of vitamin $B_6$+2 g of vitamin C (the vitamins were added to 250 mL of a 0.9% sodium chloride injection) were slowly infused intravenously at a rate of 30 to 60 drops per minute, and functional rehabilitation exercises were performed. The patient had clear consciousness after 18 days, the motion of both upper limbs was good, somatesthesia was significantly improved, and the muscle tone of both lower limbs was slightly improved. The patient is now in treatment.

What is claimed is:

1. A method for treating a subject having acute myelitis, comprising
administering a pharmaceutical composition to the subject having acute myelitis,
wherein the pharmaceutical composition comprises 0.5 to 8 g of L-ornithine, 1 to 5 g of aspartic acid, 3 to 10 g of arginine, 3 to 10 g of vitamin $B_6$, with the rest being an excipient and/or other ingredients.

2. The method according to claim 1, wherein the pharmaceutical composition further comprises one or more substances selected from the group consisting of isoleucine, leucine, lysine, methionine, phenylalanine, threonine, tryptophan, valine, histidine, glycine, alanine, proline, asparagine, cysteine, glutamic acid, serine, tyrosine, vitamin $B_1$, vitamin $B_2$, pantothenic acid, biotin, folic acid, vitamin $B_{12}$, and vitamin C.

3. The method according to claim 1, wherein the pharmaceutical composition further comprises 3 to 10 g of isoleucine, 5 to 15 g of leucine, 3 to 10 g of lysine, 0.5 to 3 g of methionine, 0.5 to 3 g of phenylalanine, 3 to 10 g of threonine, 0.5 to 3 g of tryptophan, 5 to 15 g of valine, 3 to 8 histidine g, 3 to 8 g of glycine, 3 to 10 g of alanine, 3 to 8 g of proline, 0.1 to 3 g of asparagine, 0.1 to 3 g of cysteine, 3 to 10 g of glutamic acid, 0.5 to 5 g of serine, and 0.1 to 3 g of tyrosine; and the contents of the B vitamins are: 1 to 2 mg vitamin $B_1$, 1 to 2 mg vitamin $B_2$, 3 to 5 mg pantothenic acid, 0.1 to 0.2 mg of biotin, 0.1 to 0.4 mg of folic acid, 2 to 6 μg of vitamin $B_{12}$, and 1 to 3 g of vitamin C.

4. The method according to claim 1, wherein the composition further comprises vitamin C.

5. The method according to claim 4, wherein the composition further comprises one or more of vitamin $B_1$, vitamin $B_2$, and vitamin $B_{12}$.

6. The method according to claim 1, wherein the pharmaceutical composition further comprises an amount of 5% glucose and sodium chloride injection, or 0.9% sodium chloride injection.

7. The method according to claim 1, wherein the pharmaceutical composition is in the form of granules, tablets, capsules, or injections.

8. The method according to claim 1, wherein the subject has inflammation indicated by increased cells in cerebrospinal fluid.

9. The method according to claim 1, wherein L-ornithine is present in the composition in an amount in a range of from 0.5 to 4.5 g.

10. The method according to claim 1, wherein vitamin $B_6$ is present in the composition in an amount in a range of from 5 to 10 g.

11. The method according to claim 1, wherein the subject is also under treatment with corticosteroids.

12. The method according to claim 1, wherein the subject is also under treatment with corticosteroids, immunoglobulin, or immunosuppressive therapy.

\* \* \* \* \*